United States Patent
Jones et al.

(10) Patent No.: US 9,005,167 B2
(45) Date of Patent: Apr. 14, 2015

(54) NON-AXIAL RETURN SPRING FOR SAFETY NEEDLE

(75) Inventors: Scott Jones, University City, MO (US); George Clark, Lewis Center, OH (US)

(73) Assignee: Covidien LP, Mansfield, MA (US)

( * ) Notice: Subject to any disclaimer, the term of this patent is extended or adjusted under 35 U.S.C. 154(b) by 1241 days.

(21) Appl. No.: 12/886,739

(22) Filed: Sep. 21, 2010

(65) Prior Publication Data

US 2011/0009832 A1 Jan. 13, 2011

Related U.S. Application Data

(62) Division of application No. 11/525,315, filed on Sep. 22, 2006, now Pat. No. 7,824,378.

(60) Provisional application No. 60/719,762, filed on Sep. 22, 2005.

(51) Int. Cl.
  *A61M 5/178* (2006.01)
  *A61M 25/06* (2006.01)
  *A61M 5/32* (2006.01)

(52) U.S. Cl.
  CPC ....... *A61M 25/0637* (2013.01); *A61M 25/0631* (2013.01); *A61M 5/3257* (2013.01); *A61M 5/3271* (2013.01); *A61M 2005/3228* (2013.01)

(58) Field of Classification Search
  CPC .................. A61M 2205/585; A61M 2205/583
  USPC .......................... 604/900, 168.01, 165.03, 177
  See application file for complete search history.

(56) References Cited

U.S. PATENT DOCUMENTS

| | | |
|---|---|---|
| 4,183,246 A | 1/1980 | Reynolds |
| 4,676,783 A | 6/1987 | Jagger et al. |
| 4,690,675 A | 9/1987 | Katz |
| 4,747,831 A | 5/1988 | Kulli |
| 4,781,692 A | 11/1988 | Jagger et al. |
| 4,813,426 A | 3/1989 | Haber et al. |
| 4,820,282 A | 4/1989 | Hogan |
| 4,900,307 A | 2/1990 | Kulli |
| 4,900,311 A | 2/1990 | Stern et al. |

(Continued)

FOREIGN PATENT DOCUMENTS

| | | |
|---|---|---|
| CN | 1447703 A | 10/2003 |
| EP | 0 139 872 A1 | 5/1985 |

(Continued)

OTHER PUBLICATIONS

English Translation of Chinese Office Action dated Jul. 2, 2010, issued in Chinese Application No. 200680042298.6, 5 pages.

(Continued)

*Primary Examiner* — Kevin C Sirmons
*Assistant Examiner* — Deanna K Hall
(74) *Attorney, Agent, or Firm* — Lisa E. Winsor, Esq.

(57) ABSTRACT

A needle safety device is provided having a housing, a needle assembly movably mounted within the housing and a spring for biasing the needle assembly within the housing. The needle assembly is movable along a first axis and the spring is movable along the second axis different from the first. There is also provided a lens for enhancing visualization of the flow of fluid through the needle safety device. There is further provided a safety sheath for covering a needle of the needle assembly and restraining the needle assembly against movement due to the bias of the spring.

13 Claims, 12 Drawing Sheets

(56) References Cited

U.S. PATENT DOCUMENTS

| | | |
|---|---|---|
| 4,973,316 A | 11/1990 | Dysarz |
| 4,994,034 A | 2/1991 | Botich et al. |
| 5,026,353 A | 6/1991 | Bartman |
| 5,084,030 A | 1/1992 | Byrne et al. |
| 5,085,639 A | 2/1992 | Ryan |
| 5,088,982 A | 2/1992 | Ryan |
| 5,108,376 A | 4/1992 | Bonaldo |
| 5,114,410 A | 5/1992 | Caralt Batlle |
| 5,120,320 A | 6/1992 | Fayngold |
| 5,125,414 A | 6/1992 | Dysarz |
| 5,129,884 A | 7/1992 | Dysarz |
| 5,147,327 A | 9/1992 | Johnson |
| 5,176,655 A | 1/1993 | McCormick et al. |
| 5,188,119 A | 2/1993 | Sunderland |
| 5,188,599 A | 2/1993 | Botich et al. |
| 5,192,275 A | 3/1993 | Burns |
| 5,215,534 A | 6/1993 | De Harde et al. |
| 5,226,894 A | 7/1993 | Haber et al. |
| 5,232,456 A | 8/1993 | Gonzalez |
| 5,267,961 A | 12/1993 | Shaw |
| 5,273,540 A | 12/1993 | Luther et al. |
| 5,312,376 A | 5/1994 | Van Heugten |
| 5,318,538 A | 6/1994 | Martin |
| 5,330,438 A | 7/1994 | Gollobin et al. |
| 5,338,303 A | 8/1994 | King et al. |
| 5,376,075 A | 12/1994 | Haughton et al. |
| 5,385,551 A | 1/1995 | Shaw |
| 5,389,076 A | 2/1995 | Shaw |
| 5,395,347 A | 3/1995 | Blecher et al. |
| 5,407,431 A | 4/1995 | Botich et al. |
| 5,409,461 A | 4/1995 | Steinman |
| 5,423,758 A | 6/1995 | Shaw |
| 5,498,243 A | 3/1996 | Vallelunga et al. |
| 5,501,675 A | 3/1996 | Erskine |
| 5,538,508 A | 7/1996 | Steyn |
| 5,549,571 A | 8/1996 | Sak |
| 5,554,130 A | 9/1996 | McDonald et al. |
| 5,562,629 A | 10/1996 | Haughton et al. |
| 5,562,634 A | 10/1996 | Flumene et al. |
| 5,573,510 A | 11/1996 | Isaacson |
| 5,575,777 A | 11/1996 | Cover et al. |
| 5,578,011 A | 11/1996 | Shaw |
| 5,591,138 A | 1/1997 | Vaillancourt |
| 5,632,733 A | 5/1997 | Shaw |
| 5,676,658 A | 10/1997 | Erskine |
| 5,695,475 A | 12/1997 | Best, Jr. et al. |
| 5,746,215 A | 5/1998 | Manjarrez |
| 5,779,679 A | 7/1998 | Shaw |
| 5,810,775 A | 9/1998 | Shaw |
| 5,928,199 A | 7/1999 | Nakagami |
| 5,931,815 A | 8/1999 | Liu |
| 5,951,525 A | 9/1999 | Thorne et al. |
| 5,997,512 A | 12/1999 | Shaw |
| 6,015,438 A | 1/2000 | Shaw |
| 6,056,726 A | 5/2000 | Isaacson |
| 6,080,137 A | 6/2000 | Pike |
| 6,090,078 A | 7/2000 | Erskine |
| 6,096,005 A | 8/2000 | Botich et al. |
| 6,179,812 B1 | 1/2001 | Botich et al. |
| 6,210,371 B1 | 4/2001 | Shaw |
| 6,221,055 B1 | 4/2001 | Shaw et al. |
| RE37,439 E | 11/2001 | Firth et al. |
| 6,494,863 B1 | 12/2002 | Shaw et al. |
| 6,524,276 B1 | 2/2003 | Halseth et al. |
| 6,547,762 B1 | 4/2003 | Halseth et al. |
| 6,572,584 B1 | 6/2003 | Shaw et al. |
| 6,582,402 B1 | 6/2003 | Erskine |
| 6,620,136 B1 | 9/2003 | Pressly, Sr. et al. |
| 6,641,555 B1 | 11/2003 | Botich et al. |
| 6,673,047 B2 | 1/2004 | Crawford et al. |
| 6,743,186 B2 | 6/2004 | Crawford et al. |
| 6,773,419 B2 | 8/2004 | Crawford et al. |
| 6,786,875 B2 | 9/2004 | Barker et al. |
| 6,835,190 B2 | 12/2004 | Nguyen |
| 6,860,872 B2 | 3/2005 | Teichert |
| 6,905,478 B2 | 6/2005 | Ingram et al. |
| 6,945,980 B2 | 9/2005 | Nguyen et al. |
| 6,972,002 B2 | 12/2005 | Thorne |
| 6,976,976 B2 | 12/2005 | Doyle |
| 7,037,292 B2 | 5/2006 | Carlyon et al. |
| 8,192,402 B2 * | 6/2012 | Anderson et al. .......... 604/164.1 |
| 2003/0040717 A1 | 2/2003 | Saulenas et al. |
| 2003/0078540 A1 | 4/2003 | Saulenas et al. |
| 2003/0093035 A1 | 5/2003 | Mohammed |
| 2003/0199830 A1 | 10/2003 | Nguyen |
| 2003/0220619 A1 | 11/2003 | Polidoro et al. |
| 2004/0133167 A1 | 7/2004 | Ferguson et al. |
| 2004/0193110 A1 | 9/2004 | Giambattista et al. |
| 2004/0267200 A1 | 12/2004 | Carlyon et al. |

FOREIGN PATENT DOCUMENTS

| | | |
|---|---|---|
| EP | 1 306 097 B1 | 12/2004 |
| EP | 1 221 305 B1 | 10/2005 |
| WO | WO 00/47256 A1 | 8/2000 |
| WO | WO 01/93924 A1 | 12/2001 |

OTHER PUBLICATIONS

International Search Report (Form PCT/ISA/210) (second sheet) (Apr. 2005), date of completion of the International Search is Feb. 26, 2007 and date of mailing of the International Search Report is Apr. 19, 2007 for International Application No. PCT/US06/37278, filed Sep. 22, 2006, 1 page.

Patent Examination Report No. 1 for related Australian Application No. 2012203736, Aug. 13, 2014, 6 pp.

* cited by examiner

NON-AXIAL RETURN SPRING FOR SAFETY NEEDLE

CROSS REFERENCE TO RELATED APPLICATION

This patent application is a divisional of U.S. patent application Ser. No. 11/525,315, filed Sep. 22, 2006 which claims the benefit of U.S. Provisional Application Ser. No. 60/719,762, filed Sep. 22, 2005, the entire contents of each of which are incorporated herein by reference.

BACKGROUND

1. Technical field

The present disclosure relates generally to safety needles for use in various intravenous procedures. More particularly, the present disclosure relates to a retractable safety needle having a non-axial return spring to maintain a low needle profile in relation to a patient and to a safety needle having structure to enhance visualization of flashback.

2. Background of Related Art

Hypodermic needles are used for venous access in a variety of medical procedures requiring fluid sampling, percutaneous medication injection, or other delivery to or withdrawal of fluid from a patient. Various intravenous needle assemblies are known which can generally include blood collection needles, infusion needles, hemodialysis needles, needles associated with blood collection bags, etc. Problems associated with the use of intravenous needles may include needlestick injury, stabilization of the needle relative to the implant, and difficulties arising from insertion and withdrawal of the needle from the patient.

Some of the health risks associated with hazardous needle exposure include HIV, hepatitis, and other blood-borne pathogens. Medical professionals are in danger of contracting such blood-borne pathogens from infected patients by inadvertent "needle sticks" from contaminated needles employed during medical, dental, laboratory, etc. procedures. Typically, surgical needles are extremely sharp and dangerous. Injury can occur to the operator before and after the needle has been used. As discussed above, injuries which occur after use of a needle may also infect the injured party. As such, retractable needles have been developed which safely position a surgical needle within a housing after use to prevent "needle stick" injuries from occurring with contaminated needles. Although retractable needles have proven very successful in reducing the number of "needle stick" injuries, the increased size of safety needle devices has increased the profile of the needle, thus making insertion of the needle more difficult.

Additionally, when inserting a needle into a patient's arm it is desirable to be able to see the flow of blood through the needle to ensure it has been properly positioned within a vein. Visualization of blood flow through a needle is typically termed "flashback" and is often difficult to see.

Accordingly, it would be desirable to have a needle having a sheath to protect the user prior to insertion of the needle into a patient and a retraction mechanism which shields the needle after it has been removed from a patient yet does not effect the profile of the needle prior to insertion into a patient. Additionally, it would also be desirable to have a device to enhance visualization of flashback to ensure proper positioning of the needle in a patient's arm.

SUMMARY

The presently disclosed needle safety device generally includes a housing, a needle assembly movably positioned within the housing and movable along a first axis, and a biasing spring connected to the needle assembly and movable along a second axis. In one embodiment, the needle assembly includes a hollow needle and a hub connected to a tension spring. The needle assembly is located within a first chamber of the housing and the spring is located in a second chamber of the housing. The hub includes an arm connected to the spring.

In another embodiment, the needle safety device includes a release mechanism for restraining the hub from movement due to the bias of the spring. The release mechanism includes a pair of pivoting arms engageable with the hub. The release mechanism also includes a collar positioned about the housing. The hub includes a friction member which is engageable with the housing to regulate the rate of movement of the hub within the housing due to the bias of the spring.

In one embodiment, the needle safety device includes an attachment wing affixed to the housing to secure the needle safety device to a patient.

In another embodiment, the needle safety device includes a housing, a needle assembly movably mounted within the housing, and a lens supported on or adjacent to the housing for enhanced visualization of a flow of fluid through the needle assembly. In a preferred embodiment, the lens is mounted forward of a gripping surface of the device. The needle assembly includes a hub, a needle and a fluid tube, any or all of which can include a transparent portion. In one embodiment, a portion of the hub is geometrically configured to define the lens.

In yet another embodiment, a needle safety device includes a housing, a needle assembly movably mounted within the housing, a spring mounted within the housing and engageable with the needle assembly, and a removable sheath positioned on the needle assembly. The removable sheath is positioned to grasp or frictionally engage the needle assembly with a force greater than that provided by the spring on the needle assembly to prevent inadvertent release of the needle assembly.

DESCRIPTION OF THE DRAWINGS

Embodiments of the presently disclosed safety needle device are disclosed herein with reference to the drawings, wherein.

DETAILED DESCRIPTION OF THE EMBODIMENT

Embodiments of the presently disclosed safety needle device will now be described in detail with reference to the drawings wherein like numerals designate identical or corresponding elements in each of the several views. As is common in the art, the term 'proximal" refers to a position or location on the device closer to the user or operator, i.e. surgeon or physician, while the term "distal" refers to a position or location on the device further away from the user.

Figure 1:
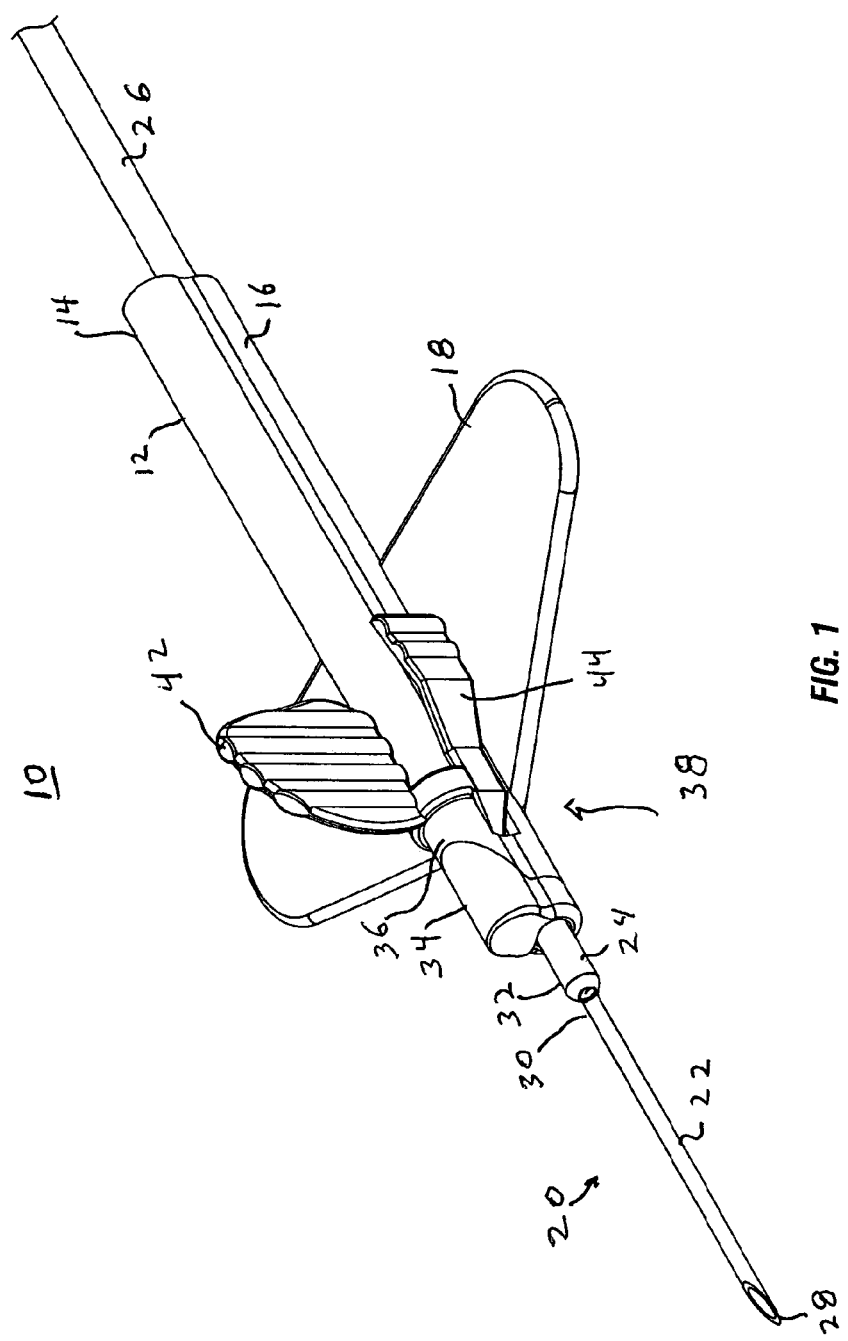
FIG. 1 is a side perspective view from the top of one embodiment of the presently disclosed safety needle device having a non-axial return spring and forward flashback visualization.
Figure 2:
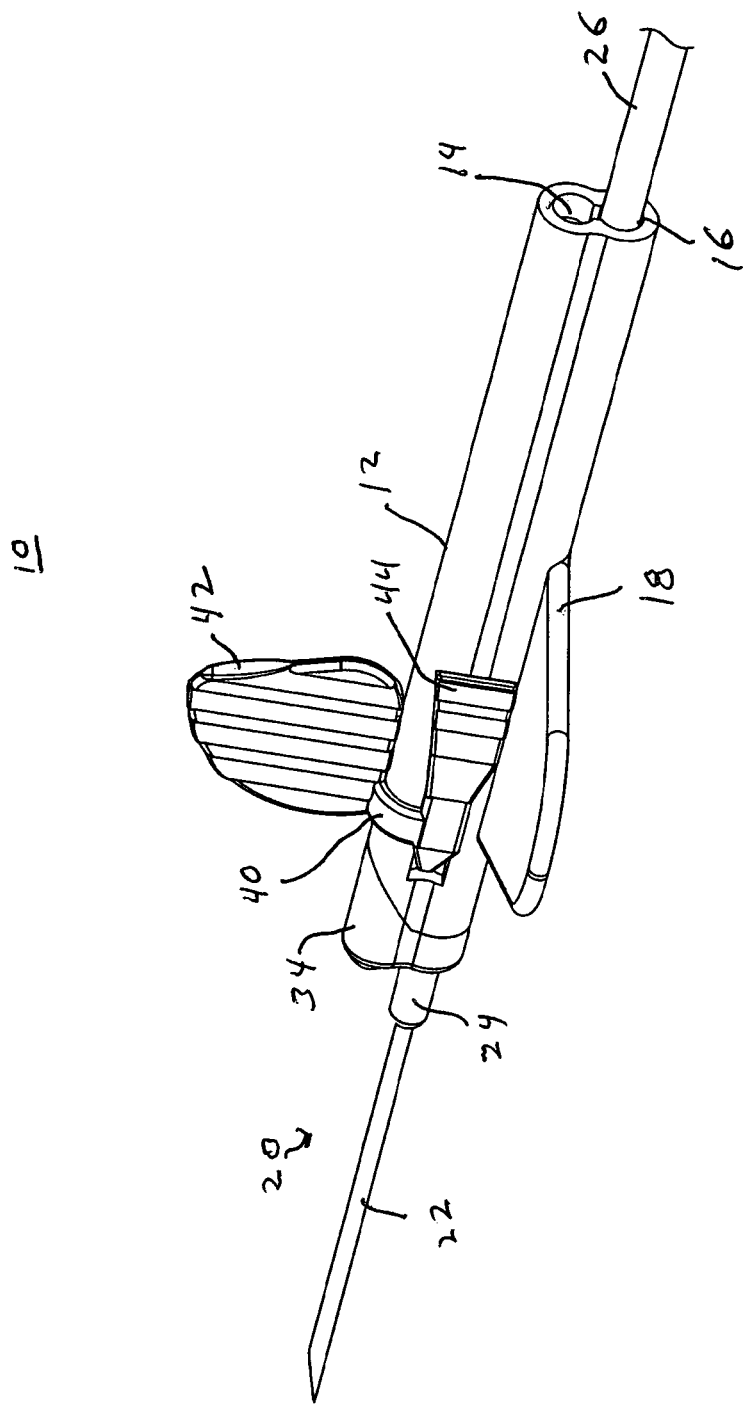
FIG. 2 is a side perspective view of the safety needle device shown in FIG. 1.

Referring initially to FIGS. 1 and 2, there is disclosed a safety needle device 10 particularly suited for use in intravenous procedures. Safety needle device 10 is constructed to prevent the possibility of needle stick injury to the user while maintaining a relatively low profile of the needle relative to the patients arm. Safety needle device 10 generally includes a housing 12 defining an upper chamber 14 and a lower chamber 16. Upper chamber 14 is configured to house a return spring defining a first longitudinal axis which is spaced from a second longitudinal axis defined by a needle 22 of device 10. One or more stabilizing wings 18 are provided on the bottom surface of housing 12 to stabilize safety needle device 10 on a patient's arm and provide an attachment point for tape or other securing mechanisms.

Safety needle device 10 also includes a needle assembly 20 movably mounted within housing 12 and having a hollow needle 22, a hub 24 and a fluid tube 26. Hollow needle 22 has a tissue penetrating needle tip 28. A proximal end 30 of hollow needle 22 is affixed to, and in fluid communication with, a distal end 32 of hub 24. In one embodiment, distal end 32 of hub 24 is transparent to allow the user to visualize the flow of fluid, i.e., blood, from hollow needle 22 after hollow needle 22 is inserted in a patient's arm. A portion of hollow needle 22 and/or fluid tube 26 may also be transparent. Blood flow through needle assembly 22 is typically termed "flashback". In order to enhance visualization of flashback, a lens 34 can be provided on or adjacent a distal end 36 of upper chamber 14 forward of or distally of a gripping surface of device 10, e.g., wings 18 or dorsal fin 42. In one embodiment, lens 34 provides a degree of magnification such that the user gets a clear indication of when the blood starts flowing through safety needle device 10. In one embodiment, a portion of hub 24 is geometrically configured to define the lens to provide enhanced and/or magnified visualization of flashback. Visualization of blood flow through needle device 10 indicates to the user that the device 10 has been properly inserted in a patient's arm.

Safety needle device 10 is also provided with a release mechanism 38 (FIG. 11) which is configured to work in conjunction with a spring 86 (FIG. 8) positioned within upper chamber 14 to control retraction of needle assembly 20 within housing 12. Release mechanism 38 includes a collar 40 which is configured to snap fit about upper chamber 14. A pair of pivoting arms 44 and 46 are formed on opposed sides of collar 40 and engage hub 24 within lower chamber 16 (FIG. 7) to retain hub 24 at an axially fixed position within housing 16. A dorsal fin 42 which facilitates guiding needle 22 during insertion into a patient's arm may be integrally formed to collar 40. Release mechanism 38 will be discussed in further detail below.

Figure 3:
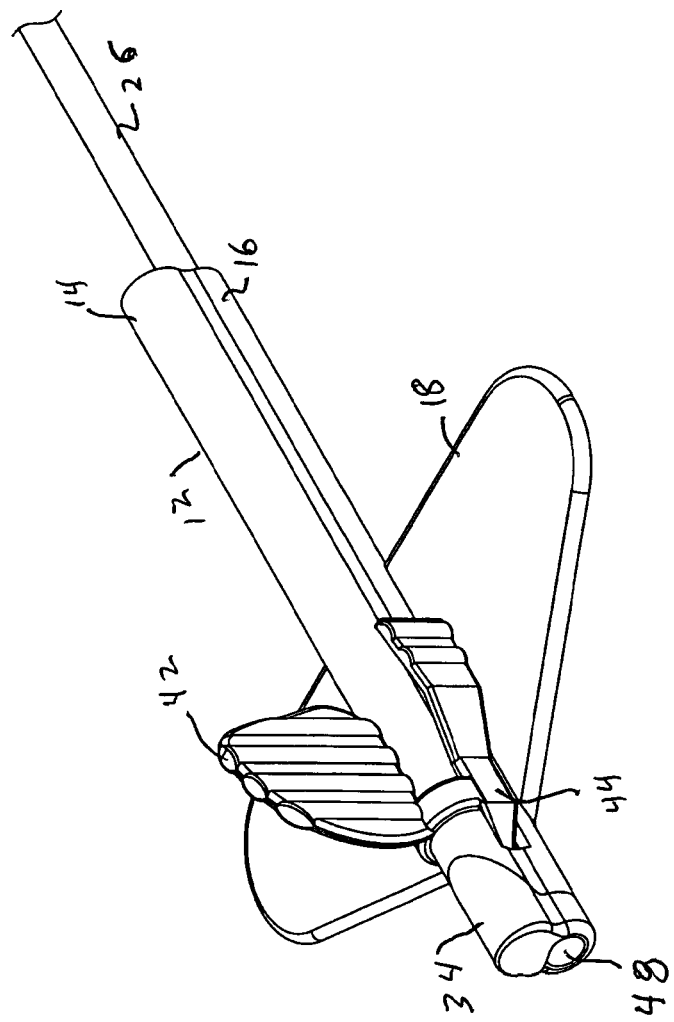
FIG. 3 is a perspective view of the safety needle device shown in FIG. 1 with the needle in a retracted position.

Referring to FIG. 3, safety needle device 10 is shown with needle assembly 20 in a retracted position. As shown, needle tip 28 does not project out of distal opening 48 of lower chamber 16 when needle assembly 20 is in the retracted position. This provides the necessary degree of safety against needle stick injury after safety needle device 10 has been removed from a patient's arm.

Figure 4:
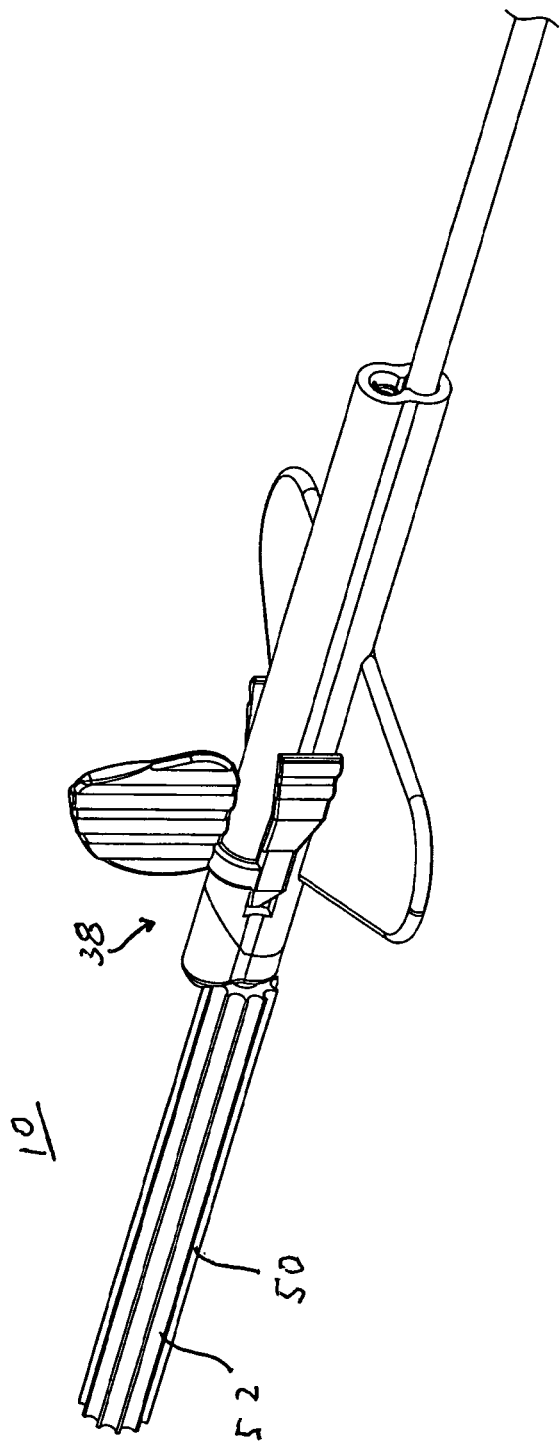
FIG. 4 is a side perspective view of the safety needle device shown in FIG. 2 with a needle sheath positioned about the needle.

With reference to FIG. 4, an additional safety feature can also be provided in the form of a sheath 50 to protect the user against needle stick injury during initial handling of safety needle device 10 and prior to use. Safety needle device 10 is designed to be shipped with protective sheath 50 surrounding needle 22. Sheath 50 is sufficiently long so that it covers needle tip 28 of hollow needle 22. In one embodiment, sheath 50 has a ribbed outer surface 52 to facilitate handling. Sheath 50 can also be configured to provide an additional function of preventing inadvertent retraction of needle assembly 20 prior to use. More specifically, sheath 50 can be designed to frictionally engage hollow needle 22 with sufficient force, i.e., a force greater than the force applied by spring 86 on hub 24, to prevent retraction of needle 22 within housing 16. Thus, activation of release mechanism 38 prior to removal of sheath 50 will not effect retraction of needle assembly 20.

Figure 5:
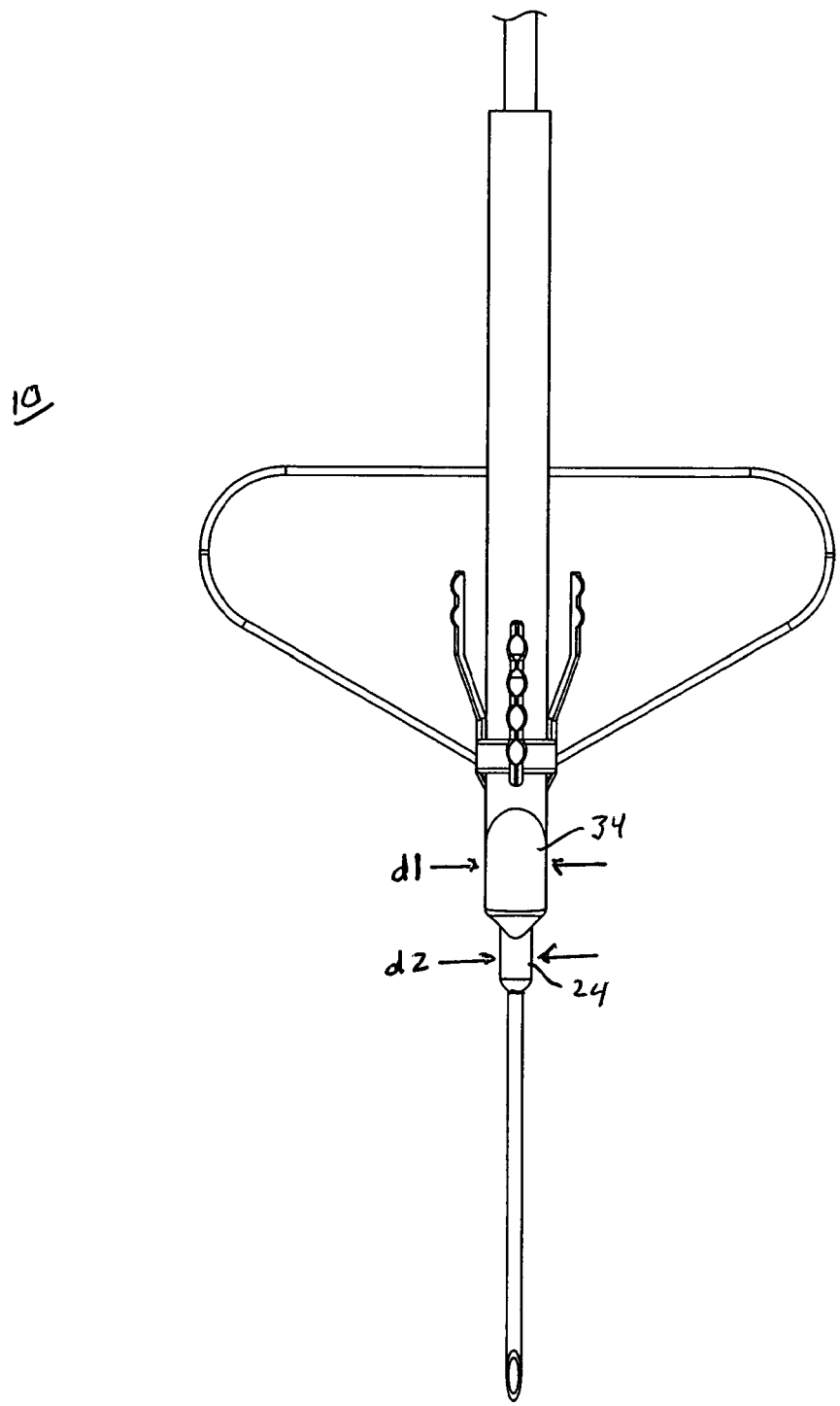
FIG. 5 is a top plan view of the safety needle device.
Figure 6:
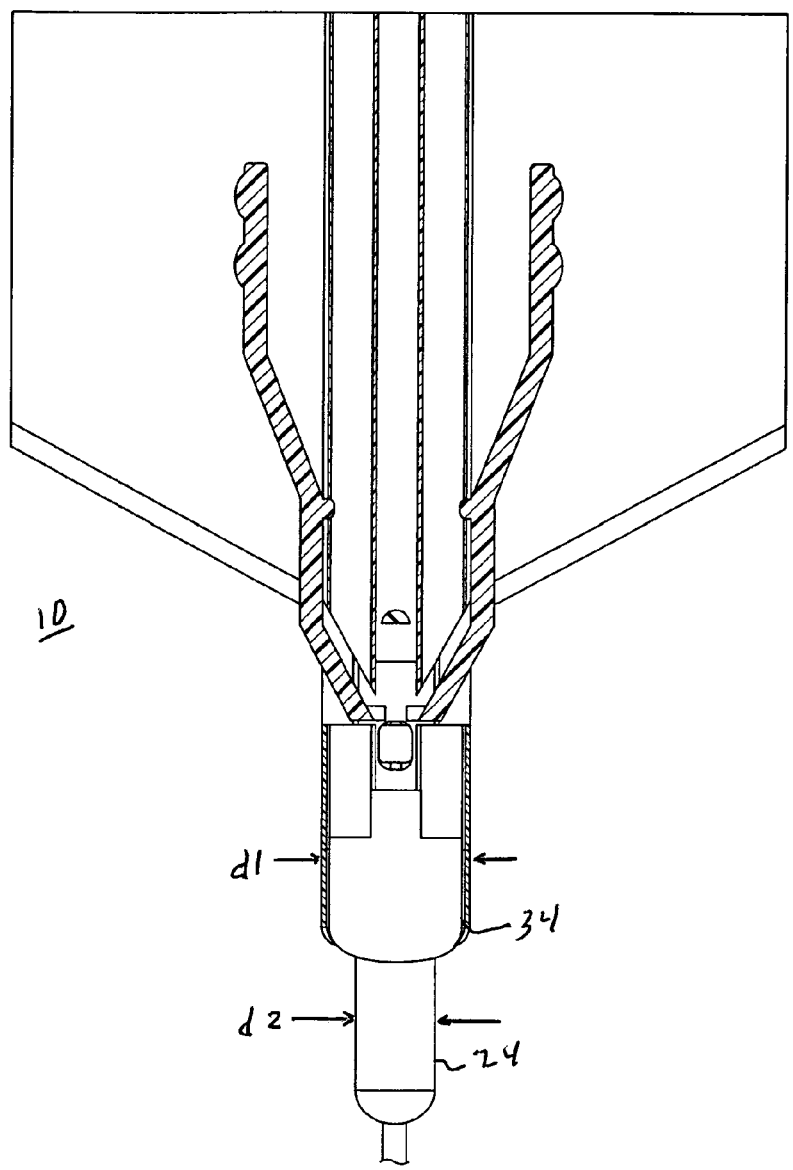
FIG. 6 is a cross-sectional view of the safety needle device and release mechanism.

Referring for the moment to FIGS. 5 and 6, it can be seen that lens 34 has a substantially larger diameter d1 than the diameter d2 of hub 24. This difference in diameters, combined with the magnification effect of lens 34, provides improved visualization of the flow of blood through safety needle device 10 at a location forward of stabilizing wings 18.

Figure 8:
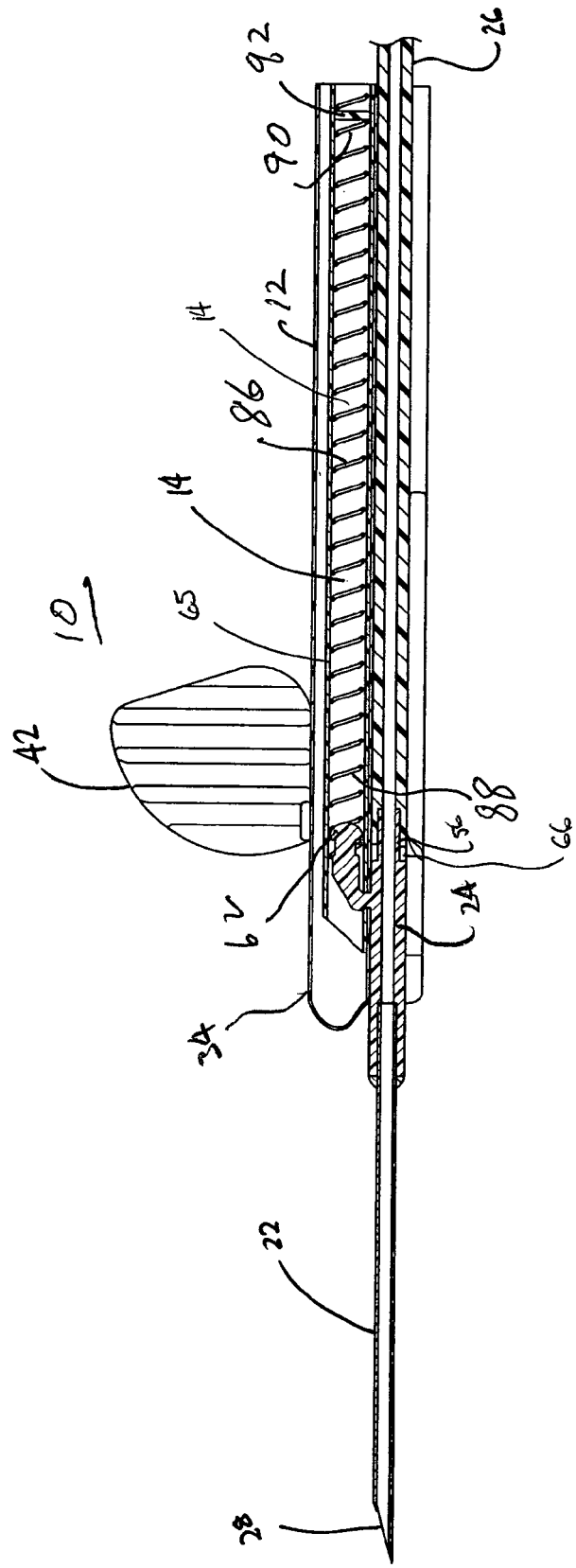
FIG. 8 is a side view, shown in section, of the safety needle device.
Figure 9:
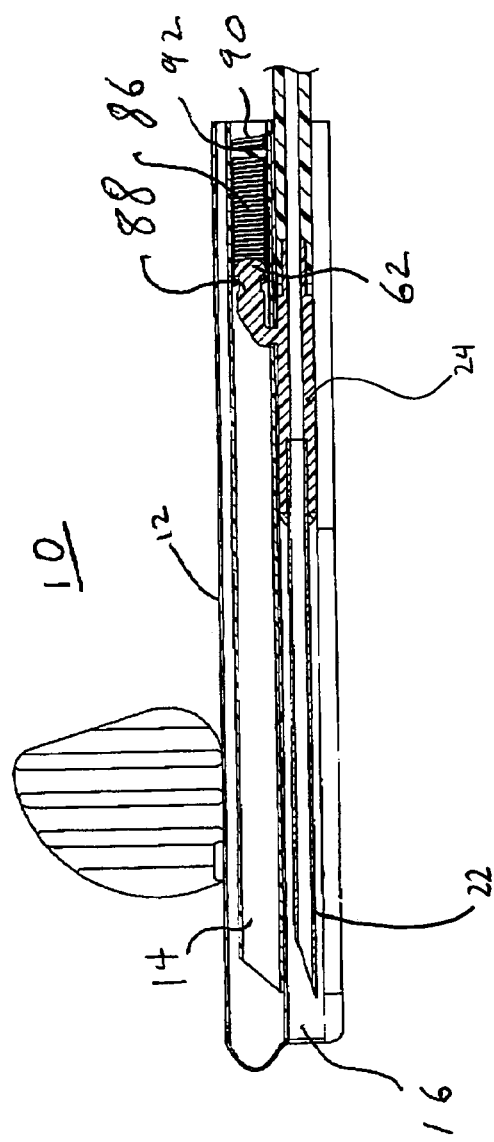
FIG. 9 is a side view, shown in section, of the safety needle device with the needle in a retracted position.
Figure 10:
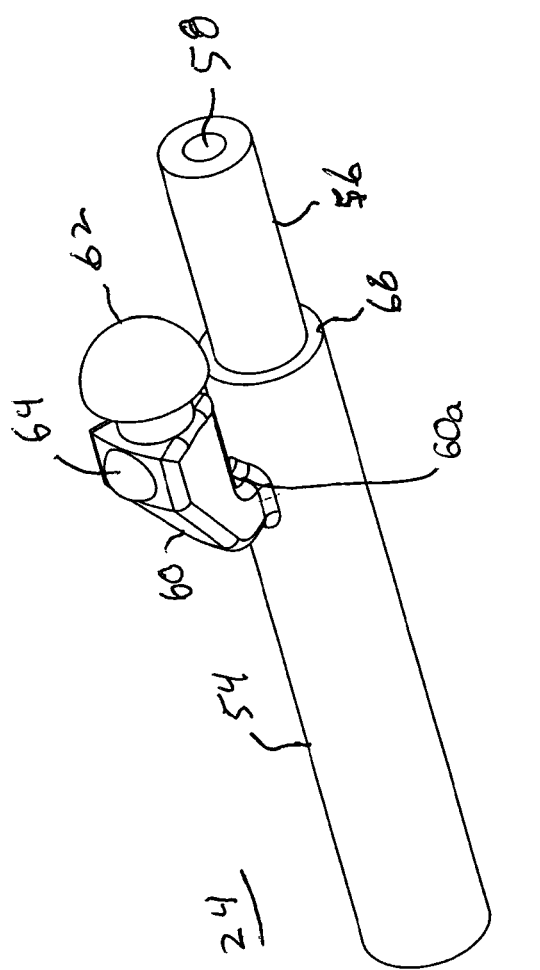
FIG. 10 is a perspective view of a hub of the safety needle device.

Referring now to FIGS. 7-12, the details of hub 24 and release mechanism 38 will now be described. With reference to FIG. 10, hub 24 includes a first portion 54 and a second reduced diameter portion 56 which together define a through-bore 58. First portion 54 is dimensioned and configured to receive and retain a proximal end of hollow needle 22 while reduced diameter portion 56 is configured to engage tube 26. Thus, tube 26 is in fluid communication with hollow needle 22. Hub 24 further includes a connecting arm 60. Connecting arm 60 is provided to engage a spring 86 (FIG. 8) located in upper chamber 14. By positioning spring 86 in an upper chamber spaced from a longitudinal axis of needle 22 and hub 24, hub 24 can freely move through lower chamber 16 and maintain a substantially lower profile than would be the case if the spring was coaxial about hub 24. Connecting arm 60 is provided with a cap 62 to engage the spring in the manner described hereinbelow.

Additionally, a protrusion 64 (FIG. 10) is formed on the surface of connecting arm 60. Protrusion 64 is positioned to frictionally engage an inner surface a spring tube 65 positioned within upper chamber 14 of housing 12 to control the rate of retraction of hub 24 within housing 12 due to the bias of the spring. A base portion 60a of connecting arm 60 provides an abutment which serves as a latching point for engagement with release mechanism 38.

Figure 7:
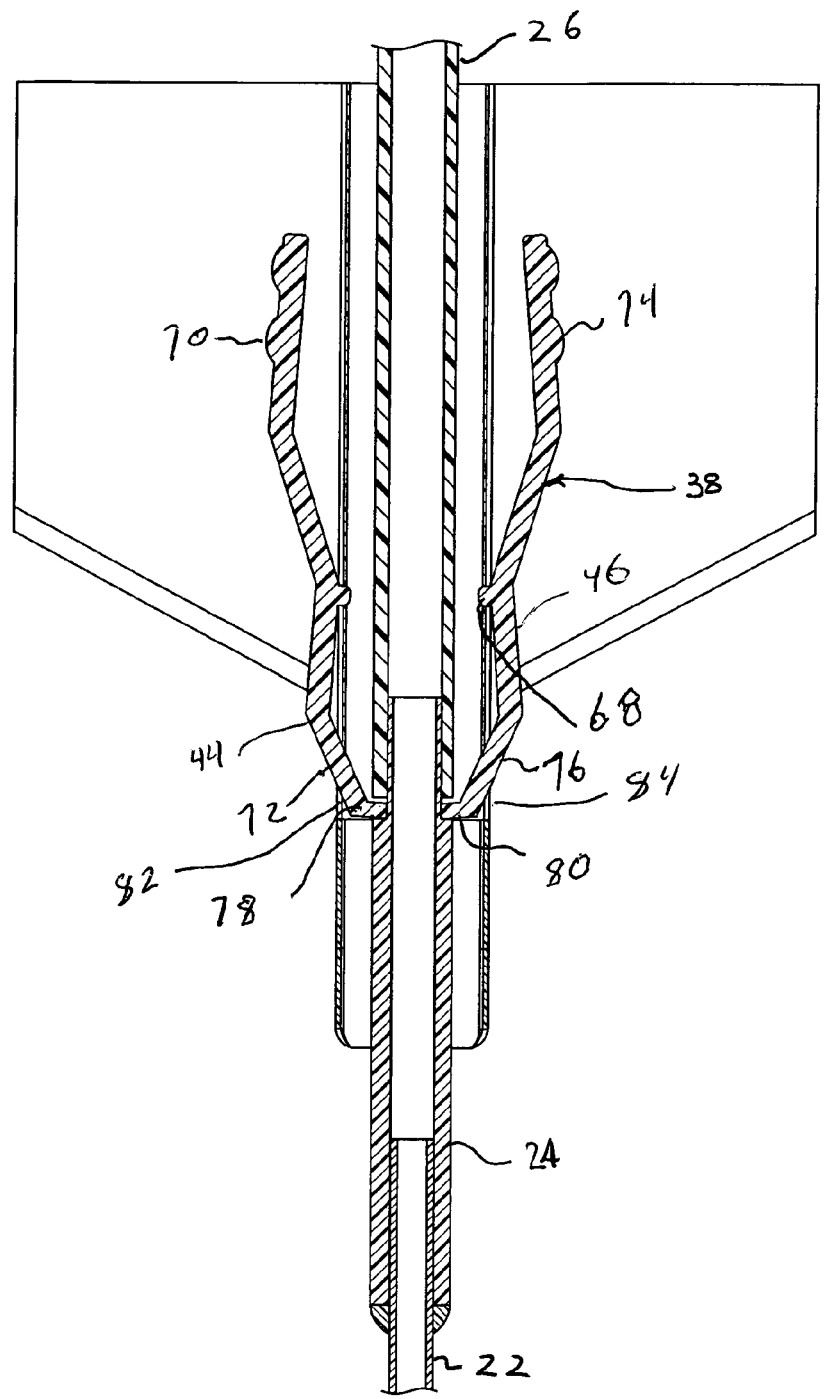
FIG. 7 is a cross-sectional view of the safety needle device and release mechanism similar to FIG. 6.
Figure 11:
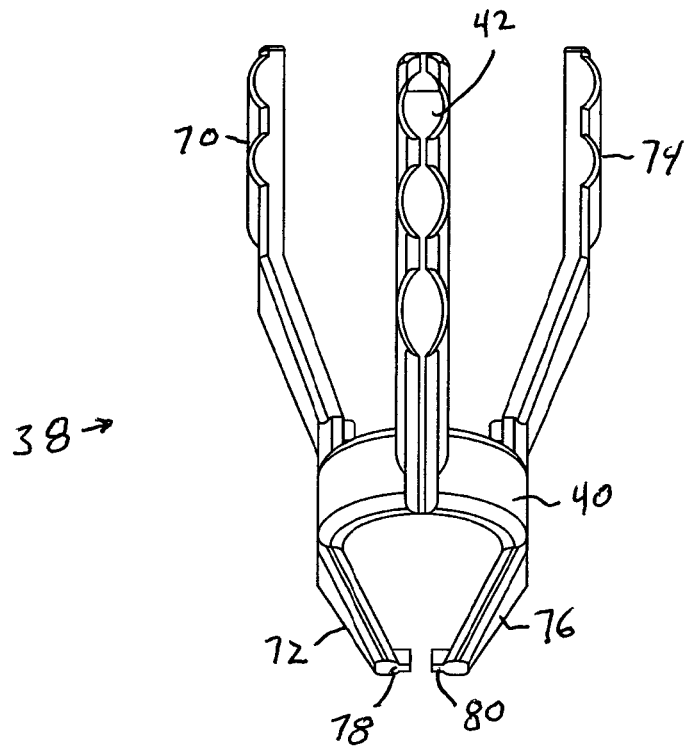
FIG. 11 is a top perspective view of the release mechanism.
Figure 12:
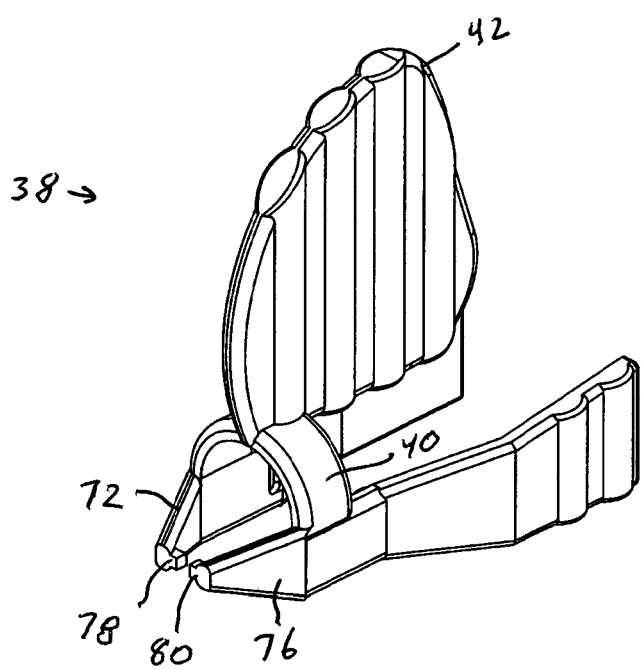
FIG. 12 is a perspective view of the release mechanism.

Referring now to FIGS. 7 and 11-12, release mechanism 38 will now be described. As noted above, release mechanism 38 includes pivoting arms 44 and 46 which are connected to collar 40. A protrusion 68 on an inner surface of collar 40 serves as a pivot point against housing 12. Pivoting arm 44 includes a proximal portion 70 and a distal portion 72. Proximal portion 70 is configured to be engaged by the fingers of the user while distal portion 72 includes a finger 80 which is configured to be received within a slot 66a defined between interface 66 and a distal end of tube 26. Similarly, pivoting arm 46 includes a proximal portion 74 and a distal portion 76.

A finger 78 is provided on distal portion 72 of pivoting arm 44 and is also received in a respective slot 66a. Fingers 78 and 80 are configured to engage interface 66 of hub 24 to prevent retraction of hub 24 within housing 12 against the bias of spring 86. Fingers 78 and 80 extend through openings 82 and 84 in housing 12.

Referring now to FIGS. 8 and 9, as noted above, safety needle device 10 includes a spring 86 to bias hub 24 and thus hollow needle 22 to a retracted position proximally within housing 12. A distal end 88 of spring 86 is affixed to cap 62 of hub 24. Specifically, the last coil of distal end 88 of spring 86 is snap fit over cap 62 of hub 24. A proximal end 90 of spring 86 is affixed to a stud 92 formed in housing 12. As shown, by positioning spring 86 in upper chamber 14, needle assembly 22 has a substantially lower profile within housing 12 relative to the surface of the patient's skin than other known devices which employ springs.

Figure 13:
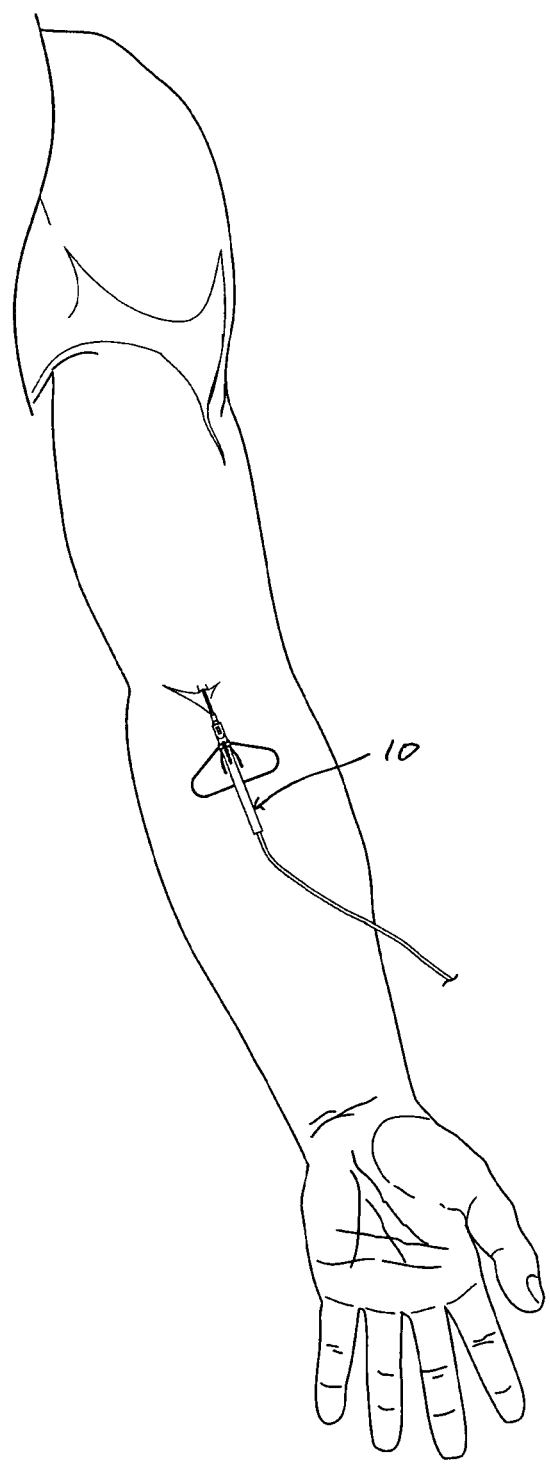
FIG. 13 is a perspective view of the safety needle device positioned on a patient's arm.

Referring to FIG. 13, safety needle device 10 is shown inserted in a patient's arm. In use, safety needle device 10 is removed from its protective packaging and sheath 50 is removed to expose hollow needle 22. As noted above, sheath 50 prevents inadvertent retraction of hollow needle 22 within housing 12 due to accidental engagement of release mechanism 38. As hollow needle 22 is inserted through a patient's skin and into a vein, visualization of the flow of blood through needle assembly 20 is greatly facilitated due to the presence of magnifying lens 34. Thus, the operator gets an immediate and easily visible indication that a vein has been penetrated and blood is flowing through safety needle device 10. After removal of safety needle device 10 from a patient release mechanism 38 is actuated by squeezing proximal portions 70 and 74 of pivoting arms 44 and 46, respectively, thereby drawing fingers 78 and 80 out of engagement with interface 66 on hub 24. Hub 24 immediately retracts within housing 12 due to the bias of spring 86. Thus, safety needle device 10 includes the safety factor of a spring powered retraction mechanism while maintaining a relatively low profile of a needle relative to a patient's skin.

It will be understood that various modifications may be made to the embodiments disclosed herein. For example, all of the disclosed embodiments of the presently disclosed needle safety device include a spring positioned in an upper chamber of a housing. Alternately, the spring can be located at other orientations, such as, for example, off to one side or the other while still maintaining a low-profile. Further, the lens may assume various other configurations. For example, the lens may be circumferential about the housing, elongate along one side of the housing etc. Moreover, all or a portion of the needle and/or hub can be transparent to facilitate visualization of flashback. Therefore, the above description should not be construed as limiting, but merely as exemplifications of particular embodiments. Those skilled in the art will envision other modifications within the scope and spirit of the claims appended hereto.

The invention claimed is:

1. A needle safety device comprising:
   a housing;
   a needle assembly movably mounted within the housing, the needle assembly having a transparent portion; and
   a lens positioned adjacent the needle assembly to enhance visualization of a flow of fluid through the transparent portion of the needle assembly.

2. The needle safety device as recited in claim 1, wherein the needle assembly includes a hub, at least a portion of the hub being transparent.

3. The needle safety device as recited in claim 1, wherein the needle assembly includes a needle, at least a portion of the needle being transparent.

4. The needle safety device as recited in claim 1, including at least one wing extending outwardly from the housing.

5. The needle safety device as recited in claim 4, wherein the transparent portion of the needle assembly is positioned forwardly of the at least one wing.

6. The needle safety device according to claim 2, wherein a portion of the hub is geometrically configured to define the lens.

7. The needle safety device according to claim 1, wherein the needle assembly includes a fluid tube, at least a portion of the fluid tube being transparent.

8. The needle safety device according to claim 1, wherein the lens is positioned on a distal end of the housing.

9. The needle safety device according to claim 1, wherein the needle assembly includes a hub, a needle and a fluid tube, and a portion of the hub is geometrically configured to define the lens.

10. The needle safety device according to claim 1, wherein the lens provides a degree of magnification to enhance visualization.

11. The needle safety device according to claim 1, wherein the needle assembly includes a hub having a first diameter, the lens having a second diameter larger than the first diameter.

12. The needle safety device according to claim 1, wherein the lens is positioned on the housing.

13. The needle safety device according to claim 1, wherein:
   the housing defines an upper chamber and a lower chamber;
   the needle assembly includes a needle hub and a hollow needle supported on and extending distally from the needle hub, the needle hub being movably positioned within the lower chamber of the housing along a first axis from an extended position wherein a distal end of the hollow needle extends from the housing to a retracted position wherein the distal end of the hollow needle is positioned within the housing; and further comprising
   a biasing spring positioned in the upper chamber and connected to the needle hub about a second axis spaced from the first axis, the biasing spring configured to bias the needle hub from the extended position to the retracted position.

* * * * *